(12) United States Patent
Kottirsch et al.

(10) Patent No.: US 6,500,983 B2
(45) Date of Patent: Dec. 31, 2002

(54) HYDROXAMIC ACID DERIVATIVES

(75) Inventors: Georg Kottirsch, Freiburg (DE); Ulf Neumann, Rheinfelden (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/973,255

(22) Filed: Oct. 9, 2001

(65) Prior Publication Data

US 2002/0038045 A1 Mar. 28, 2002

Related U.S. Application Data

(63) Continuation of application No. 09/269,867, filed on Apr. 1, 1999, now abandoned.

(30) Foreign Application Priority Data

| Oct. 2, 1996 | (GB) | ................................................ 9620572 |
| Apr. 2, 1997 | (GB) | ................................................ 9706667 |

(51) Int. Cl.[7] ...................... C07C 259/04; A61K 31/19
(52) U.S. Cl. .................... 562/621; 514/238.2; 514/352; 514/419; 514/575; 544/168; 546/309; 548/491; 562/623
(58) Field of Search ................................. 562/621, 623; 514/575, 238.2, 352, 419; 546/309; 544/168; 548/491

(56) References Cited

FOREIGN PATENT DOCUMENTS

| EP | 0 497 192 a2 | 8/1992 |
| WO | WO94/10990 | 5/1994 |
| WO | WO 95/19956 | 7/1995 |
| WO | 9519961 | * 7/1995 |
| WO | WO 96/06074 | 2/1996 |
| WO | WO 96/16931 | 6/1996 |
| WO | WO 98/33788 | 8/1998 |

* cited by examiner

*Primary Examiner*—Shailendra Kumar
(74) *Attorney, Agent, or Firm*—Carol A. Loeschorn; D. Gabrielle Brouillette

(57) ABSTRACT

Novel hydroxamic acid compounds, e.g., of formula I,

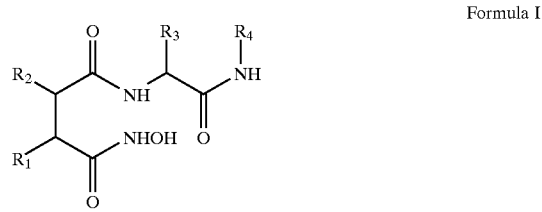

Formula I wherein $R_1$, $R_2$, $R_3$ and $R_4$ are as defined, are found to be useful as pharmaceuticals, e.g., for the suppression of TNF release and the treatment of autoimmune and inflammatory diseases, e.g., multiple sclerosis and rheumatoid arthritis. Methods of making the compounds, novel intermediates, and pharmaceutical compositions comprising the compounds are provided.

16 Claims, No Drawings

HYDROXAMIC ACID DERIVATIVES

This application is a continuation of Ser. No. 09/269,867, filed Apr. 1, 1999, now abandoned, which is a 371 of PCT/EP/97/05376, filed Sep. 30, 1997.

This invention relates to novel hydroxamic acid compounds which are useful as pharmaceuticals, e.g., in inhibiting matrix metalloproteinases such as collagenase, and in inhibiting TNF production, particularly for treatment of diseases or conditions mediated by over-production of or over-responsiveness to TNFα.

Tumor necrosis factor (TNF) is a cytokine which is produced initially as a membrane-bound 28 kD precursor. It is then cleaved by an enzyme (TNF convertase) and released as a soluble, active 17 kD form. Soluble TNF exists in at least two forms, TNFα and TNFβ, of which TNFα appears to be the more significant clinically. TNFα is believed to mediate inflammation and other conditions associated with septic shock or acute infections. Long term overstimulation by TNFα is believed to play a role in autoimmune and chronic inflammatory conditions, such as arthritis, multiple sclerosis, and the like.

It has been shown that certain matrix metalloproteinase inhibitors of the hydroxamic acid class, in particular 3-imino-4-oxo-heptane-1,7-dioic acid (7-N-hydroxy) diamides (which are optionally further 1-N-, 2-, 5-, and 6-substituted) are capable of mediating TFNα production, possibly by inhibiting TNF convertase. Known representatives of this class of compounds are summarized and described, e.g., in WO 94/10990.

It has now surprisingly been discovered that a new class of hydroxamic acid derivatives ("Novel Compounds") are potent TNFα suppressors and have advantageous pharmaceutical properties, in particular, oral bioavailability.

The Novel Compounds are 3-imino-4-oxo-6-(oxymethyl)-heptane-1,7-dioic acid (7-N-hydroxy) diamides. Suitably, the 6-oxymethyl substituent is of formula II below, e.g., hydroxymethyl or mono- or polyalkoxymethyl. The Novel Compounds may have further substitutions at the 1-N-, 2-, and 5-positions as known in the art, e.g., as described in WO 94/10990, or as further described herein. For example, the Novel Compounds may be 1-N substituted with methyl, pyridyl, or a substituent of formula X—Y— or X'—Y— as described below, e.g., 3-imino-4-oxo-6-(oxymethyl)-heptane-1,7-dioic acid (1-N-morpholinocarbonylalkyl, 7-N-hydroxy) diamide, and may be in free or pharmaceutically acceptable salt form.

A particularly preferred class of Novel Compounds are 3-imino-4-oxo-5-aryl-6-(oxymethyl)-heptane-1,7-dioic acid (7-N-hydroxy) diamides. The 5-aryl substituent may be as further described herein, e.g. wherein the 5-aryl substituent is phenyl optionally substituted, conveniently at the 4-position, e.g. by hydroxy-, $C_{1-6}$ alkyl-, $C_{1-6}$ alkoxy-, amino-, halo- or cyano-. Such 5-aryl substituted Novel Compounds may be in free or pharmaceutically acceptable salt form.

Preferably, the Novel Compounds are of Formula I

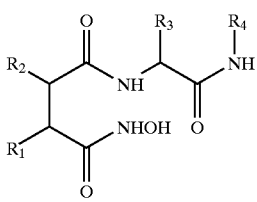

Formula I wherein
$R_1$ is a substituent of Formula II:

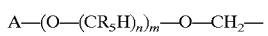

Formula II wherein
n is 1, 2, 3 or 4, preferably 2;
m is 0, 1, 2 or 3;
each $R_5$ is
  independently H, $C_{1-6}$ (optionally hydroxy-, $C_{1-6}$ alkoxy-, amino-, $C_{1-6}$ alkylamino-, thiol-, $C_{1-6}$ alkylmercapto- or protected hydroxy, amino or thiol substituted) alkyl, $C_{2-6}$ alkenyl, $C_{6-14}$ (optionally hydroxy-, $C_{1-6}$ alkoxy-, amino-, $C_{1-6}$ alkylamino-, halo- or cyano- substituted) aryl, or $C_{6-14}$ (aryl) $C_{1-6}$ alkyl; preferably H, phenyl, benzyl or $C_{1-5}$ alkyl;
A is hydrogen, $C_{1-10}$ alkyl, $C_{6-14}$ aryl, $C_{6-14}$ aryl, ($C_{1-6}$ alkyl), ($C_{6-14}$ aryl)carbonyl, or ($C_{1-10}$ alkyl) carbonyl; preferably hydrogen, $C_{1-6}$ alkyl (e.g., methyl or cyclohexyl), phenyl or benzyl;
$R_2$ is $C_{2-12}$ alkyl, $C_{3-12}$ alkenyl, $C_{3-7}$(optionally hydroxy-, $C_{1-6}$ alkoxy-, amino-, or $C_{1-6}$ alkylamino- substituted) cycloalkyl, $C_{5-14}$ aryl, or $C_{5-14}$ aryl($C_{1-6}$ alkyl), wherein aryl groups are optionally substituted by hydroxy-, $C_{1-6}$ alkyl-, $C_{1-6}$ alkoxy-, amino-, halo- or cyano-; preferably phenyl, 4-methylphenyl, 4-methoxyphenyl, cyclohexyl or isobutyl;
$R_3$ is $C_{1-10}$ (optionally hydroxy- or $C_{1-6}$ alkoxy- amino-, $C_{1-6}$ alkylamino-, thiol-, $C_{1-6}$ alkylmercapto- or protected hydroxy-, amino- or thiol- substituted) alkyl (e.g., t-butyl, or cyclohexylmethyl), $C_{6-14}$ (optionally hydroxy-, $C_{6-14}$ aryloxy-, or $C_{1-6}$ alkoxy-, amino-, $C_{1-6}$ alkylamino-, halo-, or cyano- substituted) aryl (e.g., benzyl, p-methoxybenzyl, p-benzyloxybenzyl), or indolylmethyl (e.g., 2-indolylmethyl); preferably benzyl or t-butyl;
$R_4$ is methyl, pyridyl, or a substituent of formula X—Y— wherein X is morpholino, pyridyl or aryl (preferably morpholino), and Y is $C_{1-12}$ alkylene in which up to four of the methylene (—$CH_2$—) units are optionally replaced with —CO—, —NH—, —$SO_2$— or —O—; for example methyl, 2-pyridyl, morpholinocarbonylmethyl, 5-morpholino)pentyl, or 5-(morpholinocarbonyl)pentyl.

"alkyl" includes linear, cyclic, or branched alkyl; and
"aryl" refers to an monovalent aromatic radical containing one or two aromatic rings, e.g., phenyl, benzyl, or tolyl, and includes heteroaryl containing one or more hetero atoms, e.g. N, O or S.

Halo or halogen as used herein refers to F, Cl, Br or I unless otherwise indicated.

Conveniently $R_1$ is a substituent of formula II'

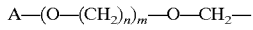

Formula II' wherein A, n and m are as defined above.

In an alternative particular embodiment $R_1$ is a substituent of formula II"

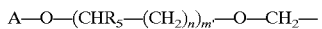

Formula II"

wherein A, n and $R_5$ are as defined above and m' is 0, 1 or 2.

When $R_4$ of formula I is a substituent of formula X—Y—, it is preferably a substituent of formula X'—Y— wherein X' is morpholino and Y is as defined above.

In particular embodiments the invention provides Novel Compounds of formula I in which independently:
n of Formula II is 3 or 4; or $R_5$ of Formula II is not H; or $R_2$ is $C_{7-12}$ alkyl, $C_{3-12}$ alkenyl, $C_{3-7}$(optionally hydroxy-, $C_{1-6}$ alkoxy-, amino-, or $C_{1-6}$ alkylamino- substituted) cycloalkyl, $C_{5-14}$ aryl, or $C_{5-14}$ aryl($C_{1-6}$ alkyl), wherein aryl groups are optionally substituted by hydroxy-, $C_{1-6}$ alkyl-, $C_{1-6}$ alkoxy-, amino-, halo- or cyano-; preferably phenyl, 4-methylphenyl, 4-methoxyphenyl or cyclohexyl; or $R_3$ is $C_{1-10}$(amino-, $C_{1-6}$ alkylamino-, thiol-, $C_{1-6}$ alkylmercapto- or protected hydroxy-, amino- or thiol- substituted)alkyl, $C_{6-14}$(amino-, $C_{1-6}$ alkylamino-, halo-, or cyano-substituted)aryl; or any aryl group thereof is heteroaryl containing one or more hetero atoms, e.g. N, O or S.

In further particular embodiments the invention provides Novel Compounds of formula I'

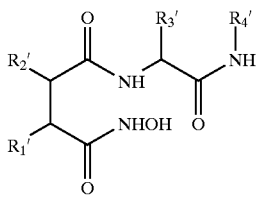

in which $R_1$' is a substituent of Formula II''':

A'—(O—(CH$_2$)$_{n'}$)$_{m'}$—O—CH$_2$—   Formula II''' such that n' is an integer one or two, preferably two;

m' is an integer zero, one, two, or three;

A' is hydrogen, $C_{6-14}$ aryl, $C_{1-10}$ alkyl, ($C_{6-14}$ aryl) carbonyl, or ($C_{1-10}$ alkyl)carbonyl, (preferably $C_{1-6}$ alkyl, e.g., methyl or cyclohexyl);

$R_2$' is $C_{2-6}$ alkyl, preferably isobutyl;

$R_3$' is $C_{1-10}$ (optionally hydroxy- or $C_{1-6}$ alkoxy-substituted) alkyl (e.g., t-butyl, or cyclohexylmethyl), $C_{6-14}$ (optionally hydroxy-, $C_{6-14}$ aryloxy-, or $C_{1-6}$ alkoxy-substituted) aryl (e.g., benzyl, p-methoxybenzyl, p-benzyloxybenzyl), or indolylmethyl (e.g., 2-indolylmethyl); preferably benzyl or t-butyl;

$R_4$' is methyl, pyridyl, or a substituent of formula X—Y— wherein X is morpholino, pyridyl or aryl (preferably morpholino), and Y is $C_{1-12}$ alkylene in which up to four of the methylene (—CH$_2$—) units are optionally replaced with —CO—, —NH—, —SO$_2$— or —O—; for example methyl, 2-pyridyl, morpholinocarbonylmethyl, 5-(morpholino)pentyl, or 5-(morpholinocarbonyl)pentyl;

Preferred Novel Compounds in which $R_2$ is aryl are compounds in which $R_1$ is of formula II' as defined above and $R_2$ is phenyl, 4-methylphenyl or 4-methoxyphenyl.

An especially preferred group of compounds of Formula I are compounds wherein:

(i) $R_1$ is of formula II' or II'' (preferably formula II') and A of formula II is hydrogen, $C_{1-6}$ alkyl, e.g., methyl or cyclohexyl (e.g., so that $R_1$ of formula I is for example hydroxymethyl, cyclohexyloxyethoxymethyl, methoxyethoxyethoxymethyl, or hydroxyethyloxymethyl) or ($C_{6-14}$ aryl)carbonyl, e.g. benzoyl (e.g. so that $R_1$ of formula I is for example benzoyloxymethyl, benzoyloxyethoxyethyl or benzoyloxyethoxymethyl);

(ii) $R_2$ of formula I is cyclohexyl, phenyl, 4-methylphenyl, 4-methoxyphenyl or isobutyl;

(iii) $R_3$ of formula I is benzyl or t-butyl; and (iv) $R_4$ of formula I is methyl or morpholinocarbonyl($C_{1-6}$)alkyl.

The Novel Compounds may exist in free or salt forms, and salt forms are intended to be encompassed by the scope of the invention. For example, certain of the Novel Compounds may exist as physiologically acceptable acid or base addition salts, e.g. as chlorhydrates, oxalates or fumarates.

The configuration of the Novel Compounds is preferably that of Formula Ia:

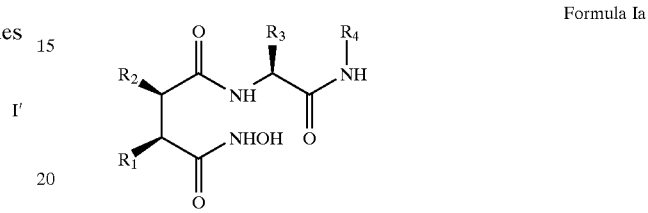

or of Formula Ib:

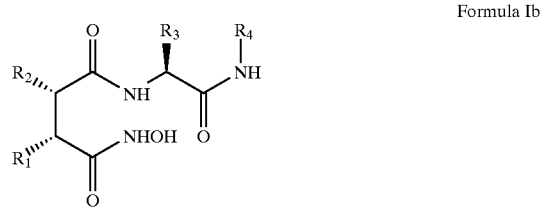

most preferably that of Formula Ia.

Thus the invention includes Novel Compounds when in the form of mixtures of enantiomers, e.g. as racemic mixtures, though preferably when in pure or substantially pure enantiomeric form, e.g. in a form in which the Novel Compound content comprises at least 90%, preferably at least 95%, and especially at least 98%, of a single isomer (i.e. comprises less than 10%, preferably less than 5%, and especially less than 2%, of other Novel Compound isomers.

In further aspects, the invention provides novel processes for the preparation of a compound of formula I or an intermediate of formulae III, IV, or V below, comprising:

a) for preparation of a compound of formula I as defined above, reacting a compound of Formula III:

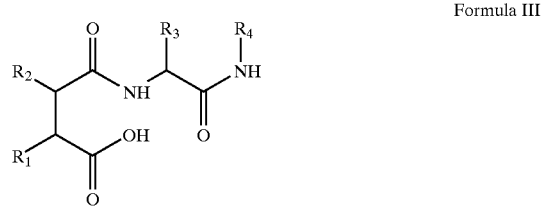

wherein $R_1$, $R_2$, $R_3$ and $R_4$ are as defined above, with hydroxylamine (optionally in salt or O— substituted form, e.g., hydroxylamine hydrochloride), recovering the product of formula I, and optionally deprotecting the product or separating the desired diastereoisomer if required;

b) for preparation of a compound of Formula III as defined above, oxidizing the olefin bond of a compound of formula IV:

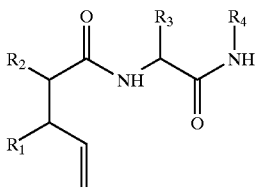

Formula IV wherein $R_1$, $R_2$, $R_3$ and $R_4$ are as defined above, e.g., using an oxidation catalyst such as ruthenium(III) chloride hydrate, to obtain the acid of Formula III, and optionally separating the desired diastereoisomer if required;

c) for preparation of a compound of formula IV, reacting a carboxylic acid of formula V $$CH_2=CH-CH(R_1)-CH(R_2)-COOH \qquad \text{Formula V}$$

wherein $R_1$ and $R_2$ are as defined above, with an amino acid amide of formula VI $$NH_2-CH(R_3)-CO-NHR_4) \qquad \text{Formula VI}$$

wherein $R_3$ and $R_4$ are as defined above, to yield an amide corresponding to formula IV, and optionally separating the desired diastereoisorner if required, and d) for preparation of a compound of formula V, reacting an alcohol of formula II$^{IV}$ $$A''-(O-(CR_5H)_n)_m-OH \qquad \text{Formula II}^{IV}$$

wherein A" is as defined above for A of formula II, except that when A is H, A" is an O-protecting group (for example a group capable of forming a readily cleavable ether, e.g., benzyl), and wherein $R_5$, n and m are as defined for Formula II above, with a dihalogenated alkene (trans), e.g., 1,4-dibromobut-2-ene, to obtain the disubstituted $R_1$, haloalkene, e.g., $R_1-CH=CH-CH_2-W$ (trans), where W is halogen, e.g., bromine, which is then reacted with a carboxylic acid corresponding to $R_2$, i.e. $R_2-CH_2COOH$, to yield the ester, which is then rearranged, e.g., in the presence of an organic base such as lithium diisopropyl amide, to give the compound of formula V.

Optionally, protecting and deprotecting steps may be included in the above described processes as necessary to preserve the integrity of the intermediates and the final product.

The invention further includes per se the novel intermediates of formulae III and IV as defined above.

As discussed in the test examples below, the Novel Compounds are potent inhibitors of TNFα release, are orally active, and are not cytotoxic at their effective doses. The Novel Compounds also inhibit collagenase and stromelysin at concentrations of from 0.3 to 10 nM. The Novel Compounds tested further show oral activity in vivo at dosages of less than 10 mg/kg in LPS induced TNFα release in the rat, and appear to be well tolerated at such dosages. Accordingly, the Novel Compounds have pharmaceutical utility as follows:

The Novel Compounds are useful for the prophylaxis and treatment of diseases or pathological conditions mediated by TNF, especially TNFα, e.g., inflammatory conditions, autoimmune diseases, severe infections, and organ or tissue transplant rejection, e.g. for the treatment of recipients of heart, lung, combined heart-lung, liver, kidney, pancreatic, skin or corneal transplants and for the prevention of graft-versus-host disease, such as following bone marrow transplants.

The Novel Compounds are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which the Novel Compounds may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

The Novel Compounds are also useful for the treatment, prevention, or amelioration of asthma, bronchitis, pneumoconiosis, pulmonary emphysema, and other obstructive or inflammatory diseases of the airways.

The Novel Compounds are useful for treating undesirable acute and hyperacute inflammatory reactions which are mediated by TNF, especially by TNFα, e.g., acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS -related cachexia, e.g., associated with or consequential to HIV infection.

In addition to inhibiting the release of TNF, especially TNFα through the suppression of TNF convertase, the Novel Compounds are also inhibitors of matrix metalloproteinases, e.g., collagenase, stromelysin and gelatinases, and hence useful for the indications known for collagenase inhibitors or other matrix metalloproteinase inhibitors, e.g., treatment of various pathological conditions of the skin, bones, and connective tissues, e.g., rheumatoid arthritis, psoriasis, psoriatic arthritis, osteoporosis, osteoarthritis, periodontitis, gingivitis, and corneal ulceration; for the treatment of cardiovascular disease, e.g., atherosclerosis, and coronary angioplasty; for the prevention of tumor cell metastasis and invasion and in inducing fibrosis of tumors, e.g., in the treatment of cancer; and for the prevention of neurodegenerative disorders, e.g., Alzheimer's disease.

For the above indications the appropriate dosage will, of course, vary depending, for example, on the particular Novel Compound employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 750 mg of Novel Compound administered orally once or, more suitably, in divided dosages two to four times/day.

The Novel Compounds may be administered by any conventional route, e.g. orally, for example in the form of solutions for drinking, tablets or capsules or parenterally, for example in the form of injectable solutions or suspensions. Normally for systemic administration oral dosage forms are preferred, although for some indications the Novel Compounds may also be administered topically or dermally, e.g. in the form of a dermal cream or gel or like preparation or, for the purposes of application to the eye, in the form of an ocular cream, gel or eye-drop preparation; or may be administered by inhalation, e.g., for treating asthma. Suitable unit dosage forms for oral administration comprise e.g. from 25 to 250 mg Novel Compound per unit dosage.

In accordance with the foregoing the present invention also provides in a further series of embodiments:

A. A method of inhibiting production of soluble TNF, especially TNFα, or of reducing inflammation in a subject (i.e., a mammal, especially a human) in need of such treatment which method comprises administering to said subject an effective amount of a Novel Compound, or a method of treating any of the above mentioned conditions, particularly a method of treating an inflammatory or autoimmune disease or condition, e.g., multiple sclerosis or rheumatoid arthritis, or alleviating one or more symptoms of any of the above mentioned conditions.

B. A Novel Compound for use as a pharmaceutical, e.g. for use as an immunosuppressant or antiinflammatory agent or for use in the prevention, amelioration or treatment of any disease or condition as described above, e.g., an autoimmune or inflammatory disease or condition.

C. A pharmaceutical composition comprising a Novel Compound in association with a pharmaceutically acceptable diluent or carrier, e.g., for use as an immunosuppressant or antiinflammatory agent or for use in the prevention, amelioration or treatment of any disease or condition as described above, e.g., an autoimmune or inflammatory disease or condition.

D. Use of a Novel Compound in the manufacture of a medicament for use as an immunosuppressant or antiinflammatory agent or for use in the prevention, amelioration or treatment of any disease or condition as described above, e.g., an autoimmune of inflammatory disease or condition.

EXAMPLE 1

Preparation of R-2-iso-Butyl-S-3-(2,5,8-trioxanonyl)-Succinic Acid-{1-[S-phenyl alanine-1-methylamide]-4-[N-hydroxyl]}-diamide (the Compound of Formula I Wherein $R_1$ is 2,5,8,-Trioxanonyl, $R_2$ is Isobutyl, $R_3$ is Benzyl, and $R_4$ is Methyl)

a. A solution of trans-1,4-dibromo-2-butene (CAS Reg. 821-06-7) (50.00 g), diethylene glycol monomethyl ether (CAS Reg. 111-77-3) (30.89 g), tetra-butylammnonium hydrogen sulfate (7.94 g) (CAS Reg. 32503-27-8) and 50% aqueous sodium hydroxide solution (113.70 ml) in methylene chloride (200 ml) is stirred at room temperature (r.t.) for 16 h. The reaction mixture is diluted with water and ether, the organic phase is separated and the product olefin is purified by chromatography.

b. A solution of the trans-olefin product of step a (27.11 g) and DBU (1,8-diazabicyclo[5.4.0]undec-7-ene, CAS Reg. 6674-22-2)(17.6 ml) in methylene chloride (200 ml) is treated with isocaproic acid (12.44 g). After one hour, anhydrous sodium carbonate (18 g) is added. The mixture is kept overnight. The organic phase is separated and the product ester is purified by chromatography.

c. A solution of LDA (lithium diisopropyl amide) in tetrahydrofuran (400 ml) is prepared at −70° C. from diisopropylamine (22.65 ml) and butyl lithium in hexane (1.6 N) (99.89 ml). A solution of the product of step b (43.90 g) in tetrahydrofuran (100 ml) is added at the same temperature. After 30 minutes, chlorotrimethylsilane (20.22 ml) is added. The temperature is raised first to room temperature then to reflux overnight. The mixture is diluted with ether. The non-acidic products are removed from the organic phase to give 35.12 g of crude acid which is then chromatographed to give 30.70 g pure carboxylic acid product.

d. A solution of the product of step c (10.50 g), (L) L-phenyl alanine-1-methyl amide (8.60 g) (e.g., preferably prepared by reacting commercially available N-carbobenzoxy (L) phenyl alanine with methylamine under standard conditions to obtain the methyl amide and hydrogenating in the presence of palladium to deprotect the amino group), and 4-dimethylaminopyridine (4.89 g) in methylene chloride (120 ml) is treated with EDCI (1-(3-dimethylaminopropyl)-3-ethylcarbodiimide hydrochloride, CAS Reg. 25952-53-8) (7.68 g) and triethyl amine (7.61 ml) and kept overnight. Ether is added, and the organic phase is dried and evaporated. The crude product, a mixture of two isomers, is chromatographed on silica gel to separate the isomers by their relative polarity.

e. The vigorously stirred solution of the less polar product of step d (5.30 g) in carbon tetrachloride (150 ml), acetonitrile (150 ml) and water (20 ml) is treated with ruthenium (III)chloride hydrate (0.49 g) and sodium perhydrate (15.16 g). Ether is added after two hours and the pH is adjusted to 4. The organic phase is separated, dried and evaporated. The residue is chromatographed on silica gel to give the pure acid.

f. A solution of the product of step e (5 g), hydroxybenzytriazole (2.00 g) and EDCI (2.51 g) in DMF (N,N-dimethyl formamide)(20 ml) is kept at room temperature for 2.5 hours. Hydroxylamine hydrochloride (1.90 g) and N-methylmorpholine (4.61 ml) are then added, and the mixture is left overnight. The solvent is evaporated under high vacuum at 50° C. The residue is purified by HPLC on RP18-silica gel to give the pure hydroxamic acid as white crystaline powder.

Melting point: 195–197° C.; Optical rotation: $[\alpha]_D^{20}$=−8.5° c=0.175 in MeOH.

EXAMPLES 2–17

The compounds corresponding to examples 2–17 of table I are prepared in analogy to example 1. The product of step c in example 1 is reacted with the the appropriate amino acid amide derivatives as decribed in step d of example 1. Following the procedures of step e and f of example 1 give the pure hydroxamic acids.

EXAMPLES 18–32

Cyclohexylglycol is used in lieu of diethylene glycol monomethyl ether for reaction with trans-1,4-dibromo-2-butene as described in step a of example 1. Following the procedures as described in step b–f of example 1 gives the pure hydroxamic acids of example 18–32 of table I.

EXAMPLES 33 and 34

Monobenzylglycol or (2-Benzyl) glycol monbenzyl ether is used in lieu of glycol monomethyl ether for reaction with trans 1,4-dibromo-2-butene as described in step a) of Example 1. Following the same procedures as described in steps b) to f) of Example 1 gives the hydroxamic acids of formula I having a benzyl protected hydroxy group at R1. Hydrogenation in the presence of a catalytic amount of paladium or barium sulphate removes the benzyl group, thus yielding after HPLC purification on RP18 silica gel the corresponding pure compounds of formula I (see Table I).

EXAMPLES 35–59

Benzyl-alcohol is used in lieu of diethylene glycol monomethyl ether for reaction with trans-1,4-dibromo-2- butene as described in step a of example 1. Following the same procedures as described in step b–f of example 1 with appropriate adjustment of starting reagent, quantities etc. gives the hydroxamic acids of formula I having benzyloxymethyl at $R_1$. Hydrogenation in the presence of catalytic amounts of palladium on barium sulfate removes the benzyl, thus yielding, after purification on HPLC on RP18 silica gel, the pure products of example 35–59 of Table I.

TABLE I

| Ex[1] | $R_1$ | $R_2$ | $R_3$ | $R_4$ |
|---|---|---|---|---|
| 1 | $CH_3(OCH_2CH_2)_2OCH_2$ | isobutyl | benzyl | methyl |
| 2 | $CH_3(OCH_2CH_2)_2OCH_2$ | isobutyl | benzyl | 2-(morpholino)ethyl |
| 3 | $CH_3(OCH_2CH_2)_2OCH_2$ | isobutyl | benzyl | 5-(p-tosylamino)pentyl |
| 4 | $CH_3(OCH_2CH_2)_2OCH_2$ | isobutyl | benzyl | 2-(morpholino carbonyl)ethyl |
| 5 | $CH_3(OCH_2CH_2)_2OCH_2$ | isobutyl | benzyl | 2-(p-tosylamino)ethyl |
| 6 | $CH_3(OCH_2CH_2)_2OCH_2$ | isobutyl | benzyl | 1-S-(methyl-carbamoyl)ethyl |
| 7 | $CH_3(OCH_2CH_2)_2OCH_2$ | isobutyl | tert.butyl | methyl |
| 8 | $CH_3(OCH_2CH_2)_2OCH_2$ | isobutyl | tert.butyl | morpholinocarbonylmethyl |
| 9 | $CH_3(OCH_2CH_2)_2OCH_2$ | isobutyl | tert.butyl | 2-(morpholino carbonyl)ethyl |
| 10 | $CH_3(OCH_2CH_2)_2OCH_2$ | isobutyl | tert.butyl | 5-(morpholino carbonyl)pentyl |
| 11 | $CH_3(OCH_2CH_2)_2OCH_2$ | isobutyl | tert.butyl | 2-pyridyl |
| 12 | $CH_3(OCH_2CH_2)_2OCH_2$ | isobutyl | p-methoxybenzyl | methyl |
| 13 | $CH_3(OCH_2CH_2)_2OCH_2$ | isobutyl | 1-R-tert.butyloxy-ethyl | methyl |
| 14 | $CH_3(OCH_2CH_2)_2OCH_2$ | isobutyl | 1-R-benzyloxyethyl | methyl |
| 15 | $CH_3(OCH_2CH_2)_2OCH_2$ | isobutyl | 1-R-benzyloxybenzyl | methyl |
| 16 | $CH_3(OCH_2CH_2)_2OCH_2$ | isobutyl | methyl-3-indolyl | methyl |
| 17 | $CH_3(OCH_2CH_2)_2OCH_2$ | isobutyl | 1-R-hydroxyethyl | methyl |
| 18 | c-hexyl-$OCH_2CH_2OCH_2$ | isobutyl | benzyl | methyl |
| 19 | c-hexyl-$OCH_2CH_2OCH_2$ | isobutyl | benzyl | 2-pyridyl |
| 20 | c-hexyl-$OCH_2CH_2OCH_2$ | isobutyl | benzyl | 3,6-dioxa-8-oxo-9-imino 11-morpholino-undecyl |
| 21 | c-hexyl-$OCH_2CH_2OCH_2$ | isobutyl | benzyl | 5-(morpholino)pentyl |
| 22 | c-hexyl-$OCH_2CH_2OCH_2$ | isobutyl | benzyl | 4-(morpholino)butyl |
| 23 | c-hexyl-$OCH_2CH_2OCH_2$ | isobutyl | benzyl | 3,6-dioxa-8-oxo-8-morpholino-octyl |
| 24 | c-hexyl-$OCH_2CH_2OCH_2$ | isobutyl | tert.butyl | methyl |
| 25 | c-hexyl-$OCH_2CH_2OCH_2$ | isobutyl | tert.butyl | 6-imino-8-S-phenyl-octyl |
| 26 | c-hexyl-$OCH_2CH_2OCH_2$ | isobutyl | tert.butyl | 5-(Z-amino)-pentyl |
| 27 | c-hexyl-$OCH_2CH_2OCH_2$ | isobutyl | tert.butyl | 6-imino-7-oxo-10-methyl-undecyl |
| 28 | c-hexyl-$OCH_2CH_2OCH_2$ | isobutyl | tert.butyl | morpholinocarbonylmethyl |
| 29 | c-hexyl-$OCH_2CH_2OCH_2$ | isobutyl | tert.butyl | 2-pyridyl |
| 30 | c-hexyl-$OCH_2CH_2OCH_2$ | isobutyl | p-methoxybenzyl | methyl |
| 31 | c-hexyl-$OCH_2CH_2OCH_2$ | isobutyl | methyl-3-indolyl | methyl |
| 32 | c-hexyl-$OCH_2CH_2OCH_2$ | isobutyl | 1-R-tert.butyloxy-ethyl | methyl |
| 33 | HO—$CH_2CH_2OCH_2$ | isobutyl | tert.butyl | methyl |
| 34 | HO—CH(benzyl)—$CH_2OCH_2$ | isobutyl | tert.butyl | methyl |
| 35 | HO—$CH_2$ | isobutyl | benzyl | methyl |
| 36 | HO—$CH_2$ | isobutyl | tert.butyl | methyl |
| 37 | HO—$CH_2$ | isobutyl | tert.butyl | 6-imino-7-oxo-10-methyl-undecyl |
| 38 | HO—$CH_2$ | isobutyl | tert.butyl | 6-imino-8-phenyl-octyl |
| 39 | HO—$CH_2$ | isobutyl | tert.butyl | 5-(morpholino carbonyl)pentyl |
| 40 | HO—$CH_2$ | isobutyl | tert.butyl | morpholinocarbonylmethyl |
| 41 | HO—$CH_2$ | isobutyl | tert.butyl | 2-(morpholino carbonyl)ethyl |
| 42 | HO—$CH_2$ | n-propyl | tert.butyl | methyl |
| 43 | $HOCH_2$ | isopropyl | tert.butyl | methyl |
| 44 | $HOCH_2$ | cyclopropyl | tert.butyl | methyl |
| 45 | $HOCH_2$ | 3-methylbutyl | tert.butyl | methyl |
| 46 | $HOCH_2$ | cyclopentyl | tert.butyl | methyl |
| 47 | $HOCH_2$ | cyclohexyl | tert.butyl | methyl |
| 48 | $HOCH_2$ | cyclopentyl-methyl | tert.butyl | methyl |
| 49 | $HOCH_2$ | cyclohexyl-methyl | tert.butyl | methyl |
| 50 | $HOCH_2$ | 2-methoxyethyl | tert.butyl | methyl |
| 51 | $HOCH_2$ | phenyl | tert.butyl | methyl |
| 52 | $HOCH_2$ | benzyl | tert.butyl | methyl |
| 53 | $HOCH_2$ | 4-phenyl-phenyl | tert.butyl | methyl |
| 54 | $HOCH_2$ | 2-phenylethyl | tert.butyl | methyl |
| 55 | $HOCH_2$ | 2-naphthyl | tert.butyl | methyl |
| 56 | $HOCH_2$ | 3-methyl- | tert.butyl | methyl |

TABLE I-continued

| Ex[1] | R₁ | R₂ | R₃ | R₄ |
|---|---|---|---|---|
| 57 | HOCH₂ | phenyl 4-methylphenyl | tert.butyl | methyl |
| 58 | HOCH₂ | 4-methoxyphenyl | tert.butyl | methyl |
| 59 | HOCH₂ | 4-fluorophenyl | tert.butyl | methyl |

Notes to table I:
z = benzyloxycarbonyl
c-hexyl = cyclohexyl
1 = unless otherwise noted, all structures have the stereochemistry of formula Ia
2 = 1/1 mixture of diasteromers related to formula Ia and Ib All compounds are characterized by mass-spectroscopy and proton NMR spectroscopy. Table II summarizes analytical data of example 1–59

TABLE II

| Ex | ms: [M-H]* | r.t. (A/B) | m.p. | $[\alpha]_D^{20}$ |
|---|---|---|---|---|
| 1 | 482 | | 195–197 | −8.5 |
| 2 | 581.4 | 4.00 (10/90) | | |
| 3 | 707.1 | | 171–172 | −3.2 |
| 4 | 609.1 | 2.98 (15/85) | 159–161 | −1.7 |
| 5 | 665.2 | 3.35 (30/70) | 211–220 | +3.6 |
| 6 | 553.4 | 1.83 (20/80) | 197–199 | −10 |
| 7 | 448.3 | | 173–174 | −11.7 |
| 8 | 561.3 | 2.33 (15/85) | | |
| 9 | 575.3 | 2.33 (15/85) | 176–177 | −8.7 |
| 10 | 617.4 | 4.44 (15/85) | 158–160 | −4.6 |
| 11 | 511.2 | 2.87 (25/75) | 197–200 | +2.8 |
| 12 | 512.1 | | 171–172 | +1.9 |
| 13 | 511.2 | | 170–171 | +24.2 |
| 14 | 496.2 | | 141–145 | +2.8 |
| 15 | 588.2 | 3.63 (30/70) | 197–199 | −5.6 |
| 16 | 521.1 | 3.26 (20/80) | 174–176 | −15.8 |
| 17 | 436.2 | 1.34 (25/75) | 115–125 | +6.8 |
| 18 | 506 | | 207 | −7.5 |
| 19 | 569 | 10.69 (30/70) | 163–166 | |
| 20 | 750.4 | 2.07 (30/70) | | |
| 21 | 647.4 | 2.51 (30/70) | 167–170 | −3.3 |
| 22 | 633.3 | 2.27 (30/70) | | |
| 23 | 707.3 | 2.62 (30/70) | 161–163 | −3.5 |
| 24 | 472.2 | | 187–188 | −9.0 |
| 25 | 647.3 | 3.12 (30/70) | | |
| 26 | 677.2 | 6.54 (40/60) | 152-155 | −7.6 |
| 27 | 641.3 | 5.77 (35/65) | | |
| 28 | 585.1 | | | |
| 29 | 535.2 | 3.48 + 3.68 (40/60) | 185 | −3.5 |
| 30 | 536.2 | 3.38 (30/70) | 195–200 | −8.9 |
| 31 | 545.2 | 3.56 (30/70) | 160 | −16.5 |
| 32 | 516.2 | 5.61 (30/70) | 150–170 | +26.4 |
| 33 | 390.2 | 1.73 (20/80) | 185–186 | −2.8 |
| 34 | 478.2 [M-H]⁻ | 5.78 (25/75) | 120 | −13.1 |
| 35 | 380.2 | | 173–175 | −2.5 |
| 36 | 346.1 | 2.31 (10/90) | 152–155 | +2.3 |
| 37 | 515.5 | 1.92 (30/70) | 190–192 | +2.0 |
| 38 | 521.5 | 1.44 (30/70) | 173–177 | |
| 39 | 514.4 | 1.68 (20/80) | | +45.8 |
| 40 | 459 | 2.93 (20/80) | 204–206 | −23 |
| 41 | 473.3 | 1.62 (15/85) | | −3.4 |
| 42 | 332.0 | — | 144–146 | |
| 43 | 332.2 | — | 149–154 | |
| 44 | | 1.18 (10/90) | 137–141 | +12.8 |
| 45 | | | 142–145 | −11.8 |
| 46 | 358.1 | 1.65 (20/80) | 183–187 | −9.4 |
| 47 | 372.2 | 1.54 (20/80) | 128–130 | +2.0 |
| 48 | 372.1 | — | 149–153 | +7.1 |
| 49 | 386.1 | 4.02 (20/80) | 142–144 | +4.9 |
| 50 | 348.1 | 2.56 (10/90) | — | |
| 51 | 366.0 | 2.70 (10/90) | 152–155 | +20.9 |
| 52 | 380.1 | 1.92 (10/90) | 130–137 | +26.0 |
| 53 | 440.1 [M-H]⁻ | 2.99 (30/70) | 182–184 | +38.7 |
| 54 | 392 [M-H]⁻ | 2.73 (20/80) | 126–130 | +3.2 |
| 55 | 414.0 [M-H]⁻ | 3.14 (20/80) | 170–172 | −1.7 |
| 56 | 380.0 | 2.24 (20/80) | 152–153 | |
| 57 | 378.1 [M-H]⁻ | 2.13 (20/80) | 146–147 | +41.4 |
| 58 | 394.2 [M-H]⁻ | | 128–135 | +47 |
| 59 | 382.1 [M-H]⁻ | | 149–153 | +40.0 |

Notes to table II:
ms = mass spectroscopy
[M-H]* = [M-H]⁺ unless otherwise indicated
r.t. retention time in min., HPLC, C18 column
A = % solvent A: acetonitrile (100%)
B = % solvent B: water (88%) + acetonitrile (9.8%) + 10% aqu. Me₄NOH (2%) + 85% aqu. H₃PO₄ (0.2%)
m.p. = melting point in ° C.
$[\alpha]_D^{20}$ = specific optical rotation at 20° C. in methanol

TEST EXAMPLE 1

Inhibition of TNF Release

Mononuclear cells are prepared from the peripheral blood of healthy volunteers using ficoll-hypaque density separation according to the method of Hansell et al., J. Imm. Methods (1991) 145: 105. and used at a concentration of $10^5$ cells/well in RPMI 1640 plus 10% FCS. Cells are incubated with serial dilutions of the test compounds for 30 minutes at 37° C. prior to the addition of IFNγ(100 U/ml) and LPS (5 μg/ml) and subsequently further incubated for three hours. Incubation is terminated by centrifugation at 1400 RPM for 10 min. TNFα in the supernatant is measured using a commercial ELISA (Innotest hTNFα, available from Innogenetics N. V., Zwijnaarde, Belgium). Novel Compounds are tested at concentrations of from 0 to 10 μM. Exemplified compounds of formula I, especially of formula Ia, suppress TNF release in this assay with an $IC_{50}$ of from about 50 nM to about 5 μM.

TEST EXAMPLE 2

Cytotoxicity

Cytotoxicity is determined on THP1 cells (5×10⁴/well) which are incubated in the presence of IFNγ(100 U/ml)n and LPS (5 μg/ml) and presence and absence of test compound for 24 hours at 37° C. Percentages of living and dead cells are assessed by a colorimetric readout (MTT), which measures mitochondrial dehydrogenase enzymes in living cells, as described in Mosman, J. Imm. Methods (1983) 65: 55. Novel Compounds tested show less than 50% cytotoxicity at a concentration of 10 μM, showing that the Novel Compounds are not cytotoxic at concentrations sufficient to suppress TNF.

TEST EXAMPLE 3

Collagenase Inhibition

Collagenase inhibition is determined using active collagenase with the thiopeptide MMP-substrate described in Stein and Izquierdo-Martin, Arch. Biochem. Biophys. 308 (1994) pp. 274–277. Test compound is incubated with the collagenase prior to the addition of the substrate at pH 6.5, 25° C. in 2-morpholinoethanesulphonic acid (50 mM) buffer with 10 mM $CaCl_2$. The absorbance is recorded at 405 nm at regular intervals for a period of 40 minutes. The inhibitory activity of the test compound is determined as a function of the collagenase activity in the control in the presence and absence of the test compound. The Novel Compounds show significant dose dependent inhibition of collagenase at low nM concentrations, e.g., below 10 nM.

TEST EXAMPLE 4

Oral Bioavailability

The assay of the preceding example is standardized by measuring activity of varyıng known concentrations of a particular test compound and used to measure the concentration of test compound in plasma following oral administration. Test compounds are admistered orally to conscious rats at a dosage of 10 mg/kg. Blood samples are taken from the cut tip of the tail at 30, 60, 120, and 240 minutes from oral administration. The plasma is subjected to trichloroacetic acid extraction. The extract is tested in the above collagenase inhibition assay to obtain an estimate of the concentration of drug present in the plasma. The Novel Compounds show good oral bioavailability, with plasma concentrations of 300–5000 nM after 30 minutes and 50–500 nM after 240 minutes. Thus, pharmaceutically effective plama levels (as shown in Test Example 1 and 3) are readily achievable with oral administration at manageable dosages, e.g., 10 mg/kg. Moreover, the plasma levels obtained are well below the cytotoxic level, and the rats were not observed to show any adverse effects at this dosage.

What is claimed is:

1. A 3-imino-4-oxo-6-(oxymethyl)-heptane-1,7-dioic acid (7-N-hydroxy) diamide, in free or pharmaceutically acceptable salt form.

2. A 3-imino-4-oxo-5-aryl-6-(oxymethyl)-heptane-1,7-dioic acid (7-N-hydroxy) diamide, in free or pharmaceutically acceptable salt form.

3. A compound according to claim 1 of Formula I

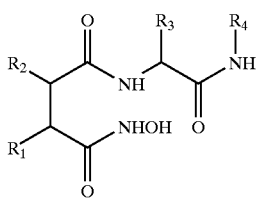

Formula I wherein $R_1$ is a substituent of Formula II:

$$A—(O—(CR_5H)_n)m—O—CH_2—$$

Formula II wherein
n is 1, 2, 3 or 4;
m is 0, 1, 2 or 3;
each $R_5$ is
independently H, $C_{1-10}$ (optionally hydroxy-, $C_{1-6}$ alkoxy-, amino-, $C_{1-6}$ alkylamino-, thiol-, $C_{1-6}$ alkylmercapto- or protected hydroxy, amino or thiol substituted) alkyl, $C_{2-6}$ alkenyl, $C_{6-14}$ (optionally hydroxy-, $C_{1-6}$ alkoxy-, amino-, $C_{1-6}$ alkylamino-, halo- or cyano- substituted) aryl, or $C_{6-14}$ (aryl) $C_{1-6}$ alkyl;

A is hydrogen, $C_{1-10}$ alkyl, $C_{6-14}$ aryl, $C_{6-14}$ aryl($C_{1-6}$ alkyl), ($C_{6-14}$ aryl)carbonyl, or $C_{1-10}$ alkyl)carbonyl;

$R_2$ is $C_{3-12}$ alkyl, $C_{3-12}$ alkenyl, $C_{3-7}$(optionally hydroxy-, $C_{1-6}$ alkoxy-, amino-, or $C_{1-6}$ alkylamino- substituted) cycloalkyl, $C_{5-14}$ aryl, or $C_{5-14}$ aryl($C_{14}$ alkyl), wherein aryl groups are optionally substituted by hydroxy-, $C_{1-6}$ alkyl-, $C_{1-6}$ alkoxy-, amino-, halo- or cyano-;

$R_3$ is $C_{1-10}$ (optionally hydroxy- or $C_{1-6}$ alkoxy-amino-, $C_{1-6}$ alkylamino-, thiol-, $C_{1-6}$ alkylmercapto- or protected hydroxy-, amino- or thiol- substituted) alkyl, $C_{6-14}$ (optionally hydroxy-, $C_{6-14}$ aryloxy-, or $C_{1-6}$ alkoxy-, amino-, $C_{1-6}$ alkylamino-, halo-, or cyano- substituted)aryl, or indolylmethyl;

$R_4$ is methyl, pyridyl, or a substituent of formula X—Y— wherein X is morpholino, pyridyl or aryl, and Y is $C_{1-12}$ alkylene in which up to four of the methylene (—$CH_2$—) units are optionally replaced with —CO—, —NH—, —$SO_2$— or —O—, in free or pharmaceutically acceptable salt form.

4. A compound according to claim 3 in which $R_1$ is a substituent of Formula II'

$$A—(O—(CH_2)_n)_m—O—CH_2—$$

Formula II' wherein A, n and m are as defined in claim 3.

5. A compound according to claim 3 in which $R_1$ is a substituent of Formula II"

$$A—O—CHR_5—(O—CH_2)_n)_m—O—CH_2—$$

Formula II"

wherein A, n and $R_5$ are as defined in claim 3 and m' is 0, 1 or 2.

6. A compound according to claim 3 with the proviso that when m of formula II, is zero, then $R_4$ of formula I is a substituent of formula X—Y—.

7. A compound of formula I as defined in claim 3 in which independently:

n of Formula II is 3 or 4; or $R_5$ of Formula II is not H; or $R_2$ is $C_{7-12}$ alkyl, $C_{3-12}$ alkenyl, $C_{3-7}$(optionally hydroxy-, $C_{1-6}$ alkoxy-, amino-, or $C_{1-6}$ alkylamino- substituted) cycloalkyl, $C_{5-14}$ aryl, or $C_{5-14}$ aryl($C_{1-6}$ alkyl), wherein aryl groups are optionally substituted by hydroxy-, $C_{1-6}$ alkyl-, $C_{1-6}$ alkoxy-, amino-, halo- or cyano-; or $R_3$ is $C_{1-10}$(amino-, $C_{1-6}$ alkylamino-, thiol-, $C_{1-6}$ alkylmercapto- or protected hydroxy-, amino- or thiol- substituted)alkyl, $C_{6-14}$(amino-, $C_{1-6}$ alkylamino-, halo-, or cyano- substituted)aryl; or any aryl group thereof is heteroaryl containing one or more hetero atoms, e.g. N, O or S.

8. A compound according to claim 3 of formula II'

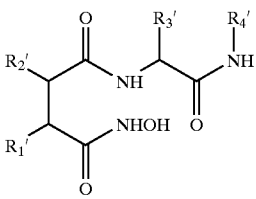

I' in which

R$_1$' is a substituent of formula II''':

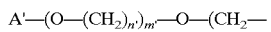
$$A'—(O—(CH_2)_{n'})_{m'}—O—(CH_2—\qquad II'''$$

such that n' is an integer one or two;

m' is an integer zero, one, two or three;

A' is hydrogen, C$_{6-14}$ aryl, C$_{1-10}$ alkyl, (C$_{6-14}$ aryl)carbonyl or (C$_{1-10}$ alkyl)carbonyl;

R$_2$' is C$_{2-6}$ alkyl;

R$_3$' is C$_{1-10}$ (optionally hydroxy- or C$_{1-6}$ alkoxy-substituted) alkyl, C$_{6-14}$ (optionally hydroxy-, C$_{6-14}$ aryloxy- or C$_{1-6}$ alkoxy-substituted) aryl or indolylmethyl;

R$_4$' is methyl, pyridyl or a substituent of formula X—Y— wherein X is morpholino, pyridyl or aryl, and Y is C$_{1-12}$ alkylene in which up to four of the methylene (—CH$_2$—) units are optionally replaced with —CO—, —NH—, SO$_2$— or —O—;

in free or pharmaceutically acceptable salt form.

9. A compound according to claim 4 wherein:

(i) R$_1$ is of formula II' and A of formula II is hydrogen, C$_{1-6}$ alkyl, or (C$_{6-14}$ aryl)carbonyl;

(ii) R$_2$ of formula I is cyclohexyl, phenyl, 4-methylphenyl, 4-methoxyphenyl or isobutyl;

(iii) R$_3$ of formula I is benzyl or t-butyl; and (iv) R$_4$ of formula I is methyl or morpholinocarbonyl(C$_{1-6}$) alkyl.

10. A compound according to claim 2 where the configuration is of formula Ia:

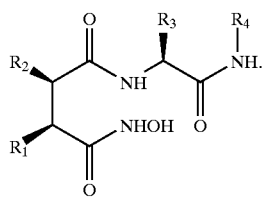

Ia

11. A method of treating an inflammatory or autoimmune disease or condition, comprising administering an effective amount of a compound according to claim 1 to a subject in need of such treatment.

12. A pharmaceutical composition comprising a compound according to claim 1.

13. A process for making a compound according to claim 1 comprising the steps of reacting a compound of Formula III

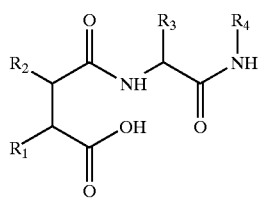

Formula III wherein

R$_1$ is a substituent of Formula II:

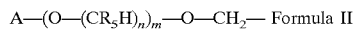
$$A—(O—(CR_5H)_n)_m—O—CH_2—\qquad \text{Formula II}$$

wherein n is 1, 2, 3 or 4;

m is 0, 1, 2, or 3;

each R$_5$ is
independently H, C$_{1-10}$ (optionally hydroxy-, C$_{1-6}$ alkoxy-, amino-, C$_{1-6}$ alkylamino-, thiol-, C$_{1-6}$ alkylmercapto- or protected hydroxy, amino or thiol substituted) alkyl, C$_{2-6}$ alkenyl, C$_{6-4}$ (optionally hydroxy-, C$_{1-6}$ alkoxy-, amino-, C$_{1-6}$ alkylamino-, halo- or cyano- substituted) aryl C$_{1-6}$ alkyl;

A is hydrogen, C$_{1-10}$ alkyl, C$_{6-14}$ aryl, C$_{6-14}$ aryl(C$_{1-6}$ alkyl), (C$_{6-14}$ aryl)carbonyl;

R$_2$ is C$_{3-12}$ alkyl, C$_{3-12}$ alkenyl, C$_{3-7}$ (optionally hydroxy-, C$_{1-6}$ alkoxy-, amino-, or C$_{1-6}$ alkylamino-substituted) cycloalkyl, C$_{5-14}$ aryl, or C$_{5-14}$ aryl(C$_{1-6}$ alkyl), wherein aryl groups are optionally substituted by hydroxy-, C$_{1-6}$ alkyl-, C$_{1-6}$ alkoxy-, amino-, halo- or cyano-;

R$_3$ is C$_{1-10}$ (optionally hydroxy- or C$_{1-6}$ alkoxy-amino-, C$_{1-6}$ alkylamino-, thiol-, C$_{1-6}$ alkylmercapto- or protected hydroxy-, amino- or thiol- substituted) alkyl, c$_{614}$ (optionally hydroxy-, C$_{6-14}$ aryloxy-, or C$_{1-6}$ alkoxy-, amino-, C$_{1-6}$ alkylamino-, halo-, or cyano- substituted) aryl, or indolylmethyl;

R$_4$ is methyl, pyridyl, or a substituent of formula X—Y— wherein X is morpholino, pyridyl or aryl, and Y is C$_{1-12}$ alkylene in which up to four of the methylene (—CH$_2$—) units are optionally replaced with CO—, —NH—, —SO$_2$— or —O—;

in free or pharmaceutically acceptable salt form, with hydroxylamine (optionally in salt or O-protected form) and, if required, deprotecting the product thus obtained.

14. The compound according to claim 1 selected from the group consisting of N(4)-(2,2-dimethyl-1-methylcarbamoyl-propyl-N(1)-hydroxy-2-hydroxymethyl-3-(4-methoxyphenyl)-succinamide, N(4)-(2,2-dimethyl-1-methylcarbamoyl-propyl-N(1)-hydroxy-2-hydroxymethyl-3-(4-methylphenyl)-succinamide, and N(4)-(2,2-dimethyl-1-methylcarbamoyl-propyl-N(1)-hydroxy-2-hydroxymethyl-3-phenyl succinamide.

15. A compound according to claim 5 wherein:

R$_1$ is of formula II'' and A of formula II is hydrogen, C$_{1-6}$ alkyl or (C$_{6-14}$ aryl)carbonyl;

R$_2$ of formula I is cyclohexyl, phenyl, 4-methylphenyl, 4-methoxyphenyl or isobutyl;

R$_3$ of formula I is benzyl or t-butyl; and

R$_4$ of formula I is methyl or morpholinocarbonyl(C$_{1-6}$) alkyl.

16. A compound according to claim 8, wherein n' is the integer two.

* * * * *

UNITED STATES PATENT AND TRADEMARK OFFICE
CERTIFICATE OF CORRECTION

PATENT NO. : 6,500,983 B2
DATED : December 31, 2002
INVENTOR(S) : Kottirsch et al.

It is certified that error appears in the above-identified patent and that said Letters Patent is hereby corrected as shown below:

Column 13,
Line 5, shoud read -- $A\text{-}(O\text{-}(CR_5H)_n)_m\text{-}O\text{-}CH_2\text{-}$ --.

Column 14,
Line 1, should read -- 8. A compound according to claim 3 of formula (I') --.
Line 3, should read -- $A\text{-}O\text{-}(CHR_5\text{-}(O\text{-}CH_2)_n)_{m'}\text{-}O\text{-}CH_2\text{-}$    Formula II" --.
Line 5, should read -- substituted) cycloalkyl, $C_{5\text{-}14}$ aryl, or $C_{5\text{-}14}$ aryl ($C_{1\text{-}6}$ --.

Column 15,
Line 10, should read -- A' is hydrogen, $C_{6\text{-}14}$ aryl, $C_{1\text{-}10}$ alkyl, ($C_{6\text{-}14}$ aryl) --.

Column 16,
Line 15, should read -- thiol substituted) alkyl, $C_{2\text{-}6}$ alkenyl, $C_{6\text{-}14}$ --.
Line 20, should read -- alkyl), $C_{6\text{-}14}$ aryl)carbonyl, or ($C_{1\text{-}10}$ alkyl)carbonyl; --.
Line 33, should read -- $C_{6\text{-}14}$ (optionally hydroxy-, $C_{6\text{-}14}$ aryloxy-, or $C_{1\text{-}6}$ --.

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

PATENT NO. : 6,500,983 B2
DATED : December 31, 2002
INVENTOR(S) : Kottirsch et al.

It is certified that error appears in the above-identified patent and that said Letters Patent is hereby corrected as shown below:

Column 13,
Line 55, shoud read -- A-(O-(CR$_5$H)$_n$)$_m$-O-CH$_2$-        Formula II --.

Column 14,
Line 5, should read -- 8. A compound according to claim 3 of formula (I') --.
Line 32, should read -- A-O-(CHR$_5$-(O-CH$_2$)$_n$)$_{m'}$-O-CH$_2$-        Formula II" --.
Line 56, should read -- substituted) cycloalkyl, C$_{5-14}$ aryl, or C$_{5-14}$ aryl (C$_{1-6}$ --.

Column 15,
Line 10, should read -- A' is hydrogen, C$_{6-14}$ aryl, C$_{1-10}$ alkyl, (C$_{6-14}$ aryl) --.

Column 16,
Line 15, should read -- thiol substituted) alkyl, C$_{2-6}$ alkenyl, C$_{6-14}$ --.
Line 20, should read -- alkyl), C$_{6-14}$ aryl)carbonyl, or (C$_{1-10}$ alkyl)carbonyl; --.
Line 33, should read -- C$_{6-14}$ (optionally hydroxy-, C$_{6-14}$ aryloxy-, or C$_{1-6}$ --.

This certificate supersedes Certificate of Correction issued July 6, 2004.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,500,983 B2
DATED : December 31, 2002
INVENTOR(S) : Kottirsch et al.

It is certified that error appears in the above-identified patent and that said Letters Patent is hereby corrected as shown below:

Column 13,
Line 55, shoud read -- A-(O-(CR$_5$H)$_n$)$_m$-O-CH$_2$-    Formula II --.

Column 14,
Line 5, should read -- substituted) cycloalkyl, C$_{5-14}$ aryl, or C$_{5-14}$ aryl (C$_{1-6}$ --.
Line 32, should read -- A-O-(CHR$_5$-(O-CH$_2$)$_n$)$_{m'}$-O-CH$_2$-    Formula II" --.
Line 56, should read -- 8. A compound according to claim 3 of formula (I') --.

Column 15,
Line 10, should read -- A' is hydrogen, C$_{6-14}$ aryl, C$_{1-10}$ alkyl, (C$_{6-14}$ aryl) --.

Column 16,
Line 15, should read -- thiol substituted) alkyl, C$_{2-6}$ alkenyl, C$_{6-14}$ --.
Line 20, should read -- alkyl), C$_{6-14}$ aryl)carbonyl, or (C$_{1-10}$ alkyl)carbonyl; --.
Line 33, should read -- C$_{6-14}$ (optionally hydroxy-, C$_{6-14}$ aryloxy-, or C$_{1-6}$ --.

This certificate supersedes Certificate of Correction issued July 6, 2004 and December 28, 2004.

Signed and Sealed this

Nineteenth Day of July, 2005

JON W. DUDAS
*Director of the United States Patent and Trademark Office*